United States Patent [19]

Müller

[11] Patent Number: 4,661,112
[45] Date of Patent: Apr. 28, 1987

[54] HIP JOINT PROSTHESIS

[75] Inventor: Maurice E. Müller, Bern, Switzerland

[73] Assignees: Sulzer Brothers Limited, Winterthur; Protek Ag, Berne, both of Switzerland

[21] Appl. No.: 707,571

[22] Filed: Mar. 4, 1985

[30] Foreign Application Priority Data

Mar. 6, 1984 [CH] Switzerland ............... 1094/84

[51] Int. Cl.⁴ .................................. A61F 2/32
[52] U.S. Cl. ........................................ 623/22
[58] Field of Search ............ 3/1.9, 1.91, 1.911, 3/1.912, 1.913; 128/92 C, 92 B; 623/22.23

[56] References Cited

U.S. PATENT DOCUMENTS

| | | | |
|---|---|---|---|
| 3,466,670 | 9/1969 | Christiansen | 3/1.913 |
| 3,869,731 | 3/1975 | Waugh et al. | 3/1.911 |
| 3,987,499 | 10/1976 | Scharbach et al. | 3/1.913 |
| 4,012,796 | 3/1977 | Weisman et al. | 3/1.91 |
| 4,310,931 | 1/1982 | Muller | 3/1.913 |
| 4,430,761 | 2/1984 | Niederer et al. | 128/92 C |

Primary Examiner—Richard J. Apley
Assistant Examiner—David J. Isabella
Attorney, Agent, or Firm—Kenyon & Kenyon

[57] ABSTRACT

A ruff or collar is positioned on the hip joint prosthesis shank prior to insertion of a prosthesis into a bone. The ruff can be slipped onto the straight shank in the direction of the longitudinal axis from the distal. The ruff is fixed to the transition region between the shank and the prosthesis neck by means of conical clamping surfaces.

A set of ruffs may be provided each of which has a different thickness and/or different angle between the underside bearing surface and the top surface to accommodate inaccuracies in a resection cut.

14 Claims, 5 Drawing Figures

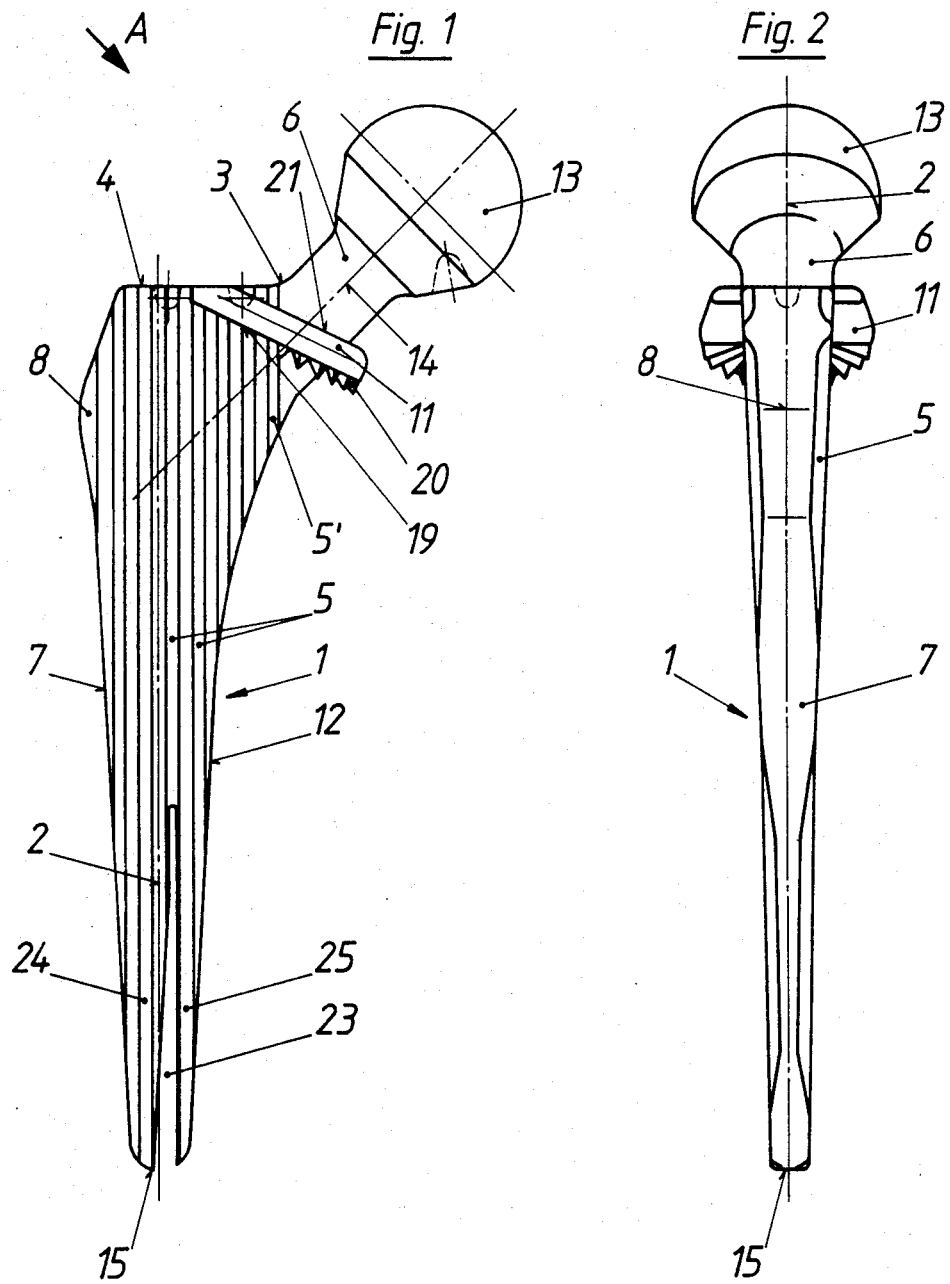

4,661,112

HIP JOINT PROSTHESIS

This invention relates to a hip joint prosthesis.

As is known, hip joint prostheses have sometimes been constructed to receive a ruff or collar which can be slipped onto a shank of the prosthesis. Such constructions have been known, for example, from German OS No. 3216538 which describes a hip joint prosthesis having a straight conically widening blade type shank which has a rib structure on the blade sides at least in the proximal shank portion which is parallel to the longitudinal axis of the shank and on which a ruff can be slipped onto the shank. The removability of the ruff is such as to facilitate extraction of the shank out of a bone into which the prosthesis has been inserted in those cases where a re-operation is required. In this respect, the removable ruff is usually pushed from the medial to the lateral onto the prosthesis shank after the shank has been completely inserted into a femur bone.

If a prothesis shank which is to be anchored in a femur bone is to be further supported on the edge of a surgical opening by means of the ruff or collar, effective support requires that the bearing surface of the ruff and the resection plane at the neck of the prosthesis must be parallel to each other to the extent possible. Moreover, the bearing surface of the ruff must have the "correct" height with respect to a reference point so that when the prosthesis is inserted, the articular head, for example, is held at the proper level relative to the trochanter. Where conventional prostheses are used, these two requirements require that the resectional cut must be made very exactly at the correct height and at the correct angle so that the work of the surgeon is made more difficult.

Accordingly, it is an object of the invention to accommodate inaccuracies in the position of a resection cut or a hip joint prosthesis.

It is another object of the invention to be able to correct for inaccuracies in the position of a resection cut for a hip joint prosthesis.

Briefly, the invention provides a hip joint prosthesis with a ruff or collar which is slidably mounted on the prosthesis. The prosthesis is constructed with a straight conically widening blade type shank, a neck, a transition region between the shank and the neck and a plurality of grooves on the shank adjacent the transition region and in parallel to a longitudinal axis of the shank. The ruff is provided with an insertion opening disposed about the transition region and is slidably mounted in a direction parallel to the longitudinal axis of the shank and distally of the shank, i.e. the ruff can be slid onto the shank from the distal end. Thus, a standard prosthesis which may optionally be used without a ruff or, respectively, with a certain shank size, may be supplied with a whole set of ruffs each of which may have different thicknesses. In addition, each ruff of a set of ruffs may have a bearing surface which is intended to rest on a prepared bone formed at a different angle with respect to the prosthesis neck axis. From such a set of ruffs, a surgeon can, after a resection has been made, select a ruff best suited for implantation and, thereafter, individually slip the ruff onto the shank of a hip joint prosthesis in the direction of the longitudinal axis of the shank. Thereafter, as the shank is driven into a femur bone, the ruff can be fixed on the shank.

In order to secure fixation of the ruff to the shank, a conical clamping seat can be provided in the transition region of the prosthesis in order to engage the ruff. Advantageously, this clamping can be provided in a groove-free portion of the transitional region. Furthermore, driving in of the shank which is effected by jamming substantially along its conical extent, and the fixation of the ruff, can be facilitated by providing a horizontal shoulder on the prosthesis at the proximal shank end and by providing a pair of driving bores in the shoulder. In this case, one of the bores is disposed adjacent the longitudinal axis of the shank while the other bore is disposed medially adjacent the prosthesis neck, i.e. near the transition of the shoulder into the prosthesis neck as far as possible toward the medial. The medially located bore serves primarily for the purpose of wedging the ruff onto the conical clamping set in the medial transition region to the prosthesis neck.

In order to reduce the "steepness" of a resection cut and, hence, the danger of the ruff or prosthesis "slipping off" toward the medial, at least the bearing surface of the applied ruff which is intended for contact on the bone is inclined to the prosthesis neck axis by an angle differing from a right angle.

The seat of the prosthesis in or on a bone can be additionally improved if the bearing surface of the ruff intended for resting on the bone is provided with a plurality of sharp wedge type teeth at least on a medial side of the bearing surface.

These and other objects and advantages of the invention will become more apparent from the following detailed description taken in conjunction with the accompanying drawings wherein:

FIG. 1 illustrates a vental-dorsal view of a hip joint prosthesis and ruff in accordance with the invention;

FIG. 2 illustrates a view taken of the prosthesis from the left side of FIG. 1;

Figure 3:
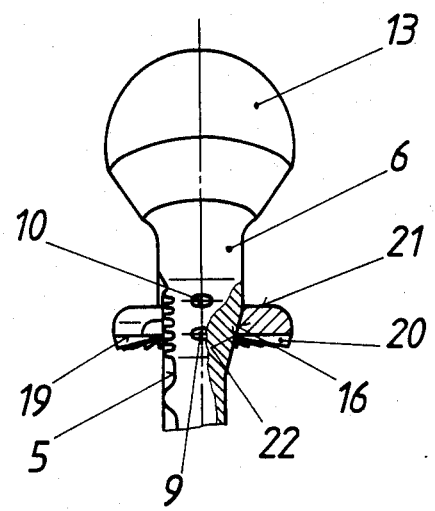
FIG. 3 illustrates a partial sectional view of the prosthesis and ruff taken in the direction indicated by the arrow A in FIG. 1.

Referring to FIGS. 1 and 2, the hip joint prosthesis has a straight blade type shank 1 which widens conically over the entire shank height as measured along a longitudinal median axis 2. In addition, the prosthesis has a neck 6 which is disposed on an axis 14 which intersects the longitudinal median axis 2 of the shank 1 at an angle which substantially corresponds to the angle between the neck of the femur (not shown) and the femur axis of a natural hip joint. In the present case, the angle of intersection is approximately 45°.

The prosthesis also has a transition region between the shank 1 and the neck 6. Also, the neck 6 carries a substantially spherical joint head 13.

The prosthesis also includes a horizontal shoulder 4, as viewed, which extends between the shank 1 and the transition region to the neck 6.

Referring to FIG. 1, the medial narrow side 12 of the prosthesis extends at first from the distal end 15 conically away from the median axis to and then changes over into an arc of a shape adapted to the calcar arc to a large extent. The likewise conically extending lateral narrow side 7 of the shank has a trochanter wing 8 which protrudes from a little above two-thirds of the shank height starting from the distal end 15. As indicated, the wing projects in an arc which is at first curved toward lateral and which ends in the horizontal shoulder 4.

Referring to FIGS. 1 and 2, the prosthesis is also provided with a plurality of grooves 5 or like surface structure, on the sides of the shank 1 which extend parallel to the longitudinal median axis 2. These grooves or surface structure serve to promote the accretion of bone tissue after implantation in a femur bone. As indicated in FIG. 1, the grooves or surface structure extend toward the medial up to a point 3 at which the shoulder 4 changes over to the transition region to the neck 6.

A ruff or collar 11 of horse-shoe shape (see FIG. 3) is slidably mounted on the prosthesis. As indicated in FIG. 5, the ruff or collar 11 has an insert opening 17 whose form and dimensions are adapted to the shank contours in the transition region between the grooves 5 and the prosthesis neck 6. To this end, a plurality of ribs 18 are disposed on opposite sides of the opening 17 which are complementary to and which mate with the grooves 5 on the shank 1 (see FIG. 4). In addition, the bearing surface or underside 19 of the ruff 11 is provided in the medial part with sharp wedge type teeth 20 for penetration into the cortical "edge" of a surgical opening.

Referring to FIG. 1, the grooves 5 in the shank 1 terminate toward the medial in a "last" groove 5' which extends from the point 3 parallel to the median axis 2 toward the distal. The "smooth" transitional region medially of this groove 5' forms a cone 16 (FIG. 3) by which the shank 1 changes over into the somewhat thicker prosthesis neck. The insert opening 17 of the ruff is provided in a mating portion with a counter-cone 22 to the cone 16 (FIG. 3).

Referring to FIG. 3, in the normal form of ruff 11 illustrated, the top and bottom surfaces 21, 19 are parallel to each other and the counter-cone 22 extends relative to the underside 19 so that the underside 19 is inclined laterally by about 20° to a plane perpendicular to the prosthesis neck axis 14 toward the distal end. Due to this, the angle of the resection plane to a horizontal plane becomes flatter, thereby reducing the danger of a ruff 11 "slipping off". Proceeding from this normal form with parallel top and bottom surfaces 21, 19, the underside 19 may enclose negative or positive angles with the top surface 21, i.e. the two surfaces may be disposed at different angles. In the case of positive angles, the two surfaces would diverge laterally and in the case of negative angles, the two surfaces would converge laterally.

Figure 4:
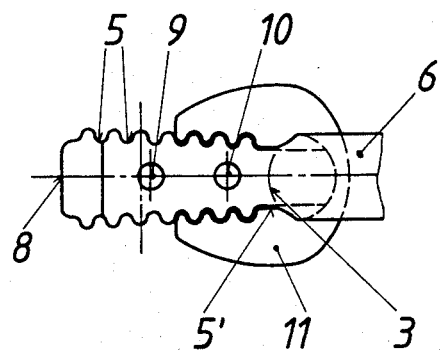
FIG. 4 illustrates a plan view of the prosthesis and ruff of FIG. 1.
Figure 5:
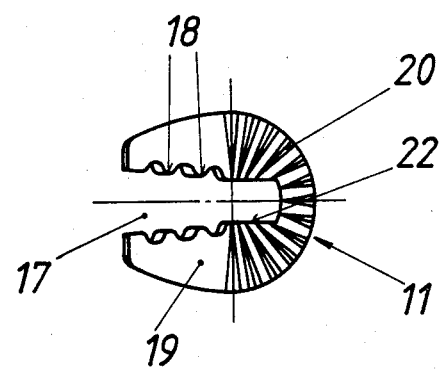
FIG. 5 illustrates an underside view of the bearing surface of a ruff in accordance with the invention.

Referring to FIGS. 3 and 4, a pair of driving bores 9,10 may be formed in the shoulder 4. As indicated in FIG. 4, one bore 9 is disposed adjacent the longitudinal axis 2 while the other bore 10 is disposed medially adjacent the neck 6. These two mutually offset driving bores 9, 10 serve for the insertion of a driving instrument (not shown). While the opening 9 near the median axis 2 serves for hammering of the shank 1 into a bone, the other bore 10 serves to secure, by means of a driving instrument (not shown) the seating of the ruff 11 on the shank 1 and a firm seating of the ruff 11 on the cortical tissue of the edge of the surgical opening (not shown).

In order to adapt the distal shank part to surgically produced cavities of different width in the femur bone, a longitudinal slit 23 is provided parallel to the median axis 2 at the distal end 15 of the shank 1. This slit 23 permits an elastic and/or plastic deformation of the distal shank part. As indicated in FIG. 1, the slit 23 is displaced toward the medial away from the median axis 2 in such a way that a lateral leg 24, despite an expansion of the slit 23 toward lateral and distal, is practically rigid and undeformable while the entire deformation occurs in a medial leg 25.

The invention thus provides a ruff or collar which can be slid onto a prosthesis shank from the distal end in parallel to the longitudinal median axis of the shank prior to implantation. Further, a whole set of ruffs or collars may be provided, each with a different thickness and/or with a different angle of inclination of an underside bearing surface so as to customize the ruff to the patient.

Further, with the ruff initially slid into place, subsequent hammering of the prosthesis into place in a bone also serves to fix the ruff in place via the mating conical surfaces 16, 21 (see FIG. 3).

Further, by providing a set of ruffs, inaccuracies in the position of a resection cut can, to some extent, be corrected. That is, the best ruff to fit the position of the resection cut can be selected.

What is claimed is:

1. In combination,
a hip joint prosthesis having a straight conically widening blade type shank, a neck, a transition region between said shank and said neck, and a plurality of grooves on said shank adjacent said transition region and in parallel to a longitudinal axis of said shank; and
a ruff slidably mounted on said shank of said prosthesis in a direction parallel to said longitudinal axis and and distally of said shank, said ruff having an insertion opening disposed about said transition region and a plurality of ribs complementary to and mating with said grooves on said shank.

2. The combination as set forth in claim 1 wherein said transition region forms a cone matingly engaging with a counter-cone on said ruff.

3. The combination as set forth in claim 2 wherein said neck is disposed on an axis inclined to said longitudinal axis and said ruff has a bearing surface for resting on a prepared bone inclined to said neck axis by an angle differing from a right angle.

4. The combination as set forth in claim 3 which further comprises a plurality of sharp wedge-shaped teeth on a side of said bearing surface to directly interface with a prepared bone.

5. The combination as set forth in claim 4 wherein said prosthesis has a shoulder between said shank and said transition region and a pair of driving bores in said shoulder, one of said bores being disposed adjacent said longitudinal axis and the other of said bores being disposed medially adjacent said neck.

6. The combination as set forth in claim 1 wherein said neck is disposed on an axis inclined to said longitudinal axis and said ruff has a bearing surface for resting on a prepared bone inclined to said neck axis by an angle differing from a right angle.

7. The combination as set forth in claim 1 wherein said ruff has a bearing surface for seating on a prepared bone and a plurality of sharp teeth on at least a side of said bearing surface to directly interface with a prepared bone.

8. The combination as set forth in claim 1 wherein said prosthesis has a shoulder between said shank and said transition region and a pair of driving bores in said shoulder, one of said bores being disposed adjacent said longitudinal axis and the other of said bores being disposed medially adjacent said neck.

9. In combination,
  a hip joint prosthesis having a straight conically widening blade type shank, a neck, a transition region between said shank and said neck, and a plurality of grooves on said shank adjacent said transition region and in parallel to a longitudinal axis of said shank; and
  a ruff having a plurality of ribs complementary to and mating with said grooves on said shank and being slidably mounted in said grooves for movement parallel to said longitudinal axis.

10. The combination as set forth in claim 9 wherein said ruff has a horse-shoe shape.

11. The combination as set forth in claim 9 wherein said transition region forms a cone matingly engaging with a counter-cone on said ruff.

12. In combination
  a hip joint prosthesis having a straight conically widening blade type shank, a neck, a transition region between said shank and said neck, and a plurality of grooves on said blade adjacent said transition region and in parallel to a longitudinal axis of said blade; and
  a set of ruffs for selective mounting on said prosthesis, each said ruff having a plurality of ribs complementary to said grooves on said shank for mating in said grooves and for slidable mounting on said shank in a direction parallel to said longitudinal axis and distally of said shank, each said ruff having an insertion opening for disposition about said transition region.

13. The combination as set forth in claim 12 wherein each ruff of said set has a different thickness.

14. The combination as set forth in claim 12 wherein each ruff of said set has a bearing surface for resting on a prepared bone at a different angle selective to said neck axis.

* * * * *